United States Patent [19]

Antoon, Jr. et al.

[11] Patent Number: 4,923,650

[45] Date of Patent: May 8, 1990

[54] BREATHABLE MICROPOROUS FILM AND METHODS FOR MAKING IT

[75] Inventors: Mitchell K. Antoon, Jr.; David J. Hill, both of Wilmington, Del.

[73] Assignee: Hercules Incorporated, Wilmington, Del.

[21] Appl. No.: 224,632

[22] Filed: Jul. 27, 1988

[51] Int. Cl.$^5$ .............................. C08J 9/32; C08J 9/36; B29C 55/12

[52] U.S. Cl. ........................................ 264/41; 55/159; 264/45.3; 264/210.7; 264/211; 264/288.8; 264/290.2; 264/DIG. 6

[58] Field of Search ..................... 264/41, 45.3, 210.7, 264/211, 288.8, 290.2, DIG. 6

[56] References Cited

U.S. PATENT DOCUMENTS 4,176,148 11/1979 Magder et al. .................. 264/288.8
4,472,328 9/1984 Sugimoto et al. .................. 524/481
4,705,812 11/1987 Ito et al. .......................... 264/288.8
4,705,813 11/1987 Ito et al. .......................... 264/288.8

Primary Examiner—Morton Foelak
Attorney, Agent, or Firm—David Edwards

[57] ABSTRACT

A soft, flexible, microporous film is provided having high tensile strength and good air and water vapor transmission rates therethrough while being substantially impenetrable to liquid water. This film is prepared by stretching a casting of a composition of a polyolefin and high levels of $CaCO_3$ or glass beads and calcium stearate in two directions from 1.5–7 times in each direction to produce a film having a Gurley porosity of from 0.1 to 85 seconds. This film is especially useful for disposable items such as feminine panty liners, diapers, bed sheets, and hospital gowns. When glass beads are substituted for the $CaCO_3$, the film is useful for battery separators.

5 Claims, No Drawings

BREATHABLE MICROPOROUS FILM AND METHODS FOR MAKING IT

BACKGROUND OF INVENTION

This invention relates to soft, flexible, microporous films having high tensile strength and good air and water vapor transmission rates therethrough but which are substantially impenetrable to liquid water. This invention also comprehends a process for making such films by stretching certain highly filled polymer compositions under controlled conditions.

Prior to the present invention, breathable microporous film were made by a variety of techniques from polymers containing solid substances dispersed therein. Sometimes the pores of the film were obtained by dissolving or leaching out those dispersed materials (fillers) and sometimes Pores were formed when the filled polymer material was stretched. Often the porous films produced by stretching the filled polymer compositions were stiff, low tear strength products, irrespective of the type of matrix polymer used. Hence, there is a need in the hygienic product industry for liquid barrier yet breathable, disposable products such as in feminine panty liners, diapers, bed sheets, and hospital gowns. In order for public acceptance of breathable products, the user should be cool and comfortable and the product has to be soft and flexible without irritating the skin of the user. There is also a need for such breathable films in the battery industry for use as battery separators. The present invention solves the above-mentioned needs.

U.S. Pat. No. 4,698,372 discloses a microporous Polymeric film having good water vapor transmission rates and hydrostatic resistance to water penetration thereof; the film has a filler loading of about 25-35 volume % of inorganic fillers such as calcium carbonate, among others, and uses an "antagonizer" such as stearic acid in order to reduce the effective surface tension of the filler to the approximate level of that of the matrix polymer. U.S. Pat. No. 3,903,234 discloses gas permeable biaxially oriented film prepared from compositions of polyolefins containing 26-50% by weight of inorganic filler particles. U. S. Pat. No. 4,176,148 discloses microporous oriented films composed of polybutene containing 3-80% by weight of inorganic fillers. British Patent 2,151,538 discloses a process for making water vapor permeable oriented film from polyolefins containing 33-83% by weight of barium sulfate filler.

None of the above prior references discloses the instant invention.

SUMMARY OF THE INVENTION

This invention is directed to a breathable film composition comprising:
- 20 to 37% by weight of a polymer or copolymer of an α-olefin having 1-8 carbons or mixtures thereof,
- 60 to 75% by weight of calcium carbonate or glass beads having particle sizes of 10 to 15 micrometers,
- 0.1 to 3% by weight of calcium stearate, and
- optionally, 0 to 2% by weight of a stabilizer, wherein moisture level in the blended composition is maintained below 700 ppm prior to forming a casting and then, based on the polymer or copolymer used, stretching the casting in 2 directions from about 1.5 to about 7 times in each direction in a temperature range of from about 20° to about 160° C. and each of the films having a Gurley porosity (based on method B, ASTM D-726) of 0.1 second to 85 seconds so that the film has good air and water vapor transmission rates but is substantially impenetrable by liquid water.

This invention also comprehends the method of preparing the breathable microporous polymeric film composition, mentioned above, by maintaining the moisture level below 700 ppm (preferably below 300 ppm) in the blended composition prior to forming a casting and then, based on the polymer or copolymer used, Stretching the casting in two directions from about 1.5 to 7 times in each direction in a temperature range of from about 20° to about 160° C.

DETAILED DESCRIPTION OF THE INVENTION

For the purpose of this invention, a high "breathability" is synonymous with low Gurley porosity number measured in seconds by ASTM D-726, Method A or Method B. ASTM D-726, Method A, measures the time (in seconds) for 100 milliliters of air to pass through one square inch of microporous film under a pressure of 4.9 inches of water. ASTM D-726, Method B, measures the time (in seconds) for ten milliliters of air to pass through one square inch of microporous film under a pressure of 12.2 inches of water. Theoretically, Gurley numbers measured by Method A are 25 times larger than Gurley numbers measured by Method B. A low Gurley number signifies that a microporous film offers little resistance to the passage of air (or humid air). Thus, Gurley number (Gurley porosity) is a simple measure of "breathability".

"Microporous" means that the film contains numerous open pores or channels leading from one surface to the opposite surface, such pores being of a size to permit air and water vapor to pass through the film while having good resistance to the penetration of liquid water. The permeance of the microporous film of this invention is greater than 30,000,000 cc/100in -day-atmosphere (or 465,000,000 cc/m$^2$-day-atmosphere).

In the present invention, a variety of materials can be selected as matrix polymers. Generally, the polyolefins are preferred. The selection of the polymeric material will be based on the desired properties of the microporous film, as for example, temperature resistance or elastic recovery. Thermoplastic, orientable polymeric materials which exhibit tensile yielding and some permanent deformation may be used. Examples of homopolymers which can be used in this invention are polypropylene (PP), polyethylene (PE), polybutylene (PB), and 4-methylpentene. Examples of copolymers are copolymers of ethylene with propylene or an α-olefin of 4-8 carbons. Processing aids, preferably calcium stearate, coat the filler particles, thus assisting in the uniform dispersion of the filler particles thereby allowing the composition to be stretched to a high degree of orientation.

In the polyproPylene/calcium carbonate system, the amount of the calcium carbonate filler should be in the range of about 60 to 70% by weight of the composition, preferably 65%. The amount of calcium stearate should be in the range of 0.1 to 3.0% by weight, preferably 0.5 to 2.0%. The biaxial orientation of the film should be in the range of from 4 to 7 times in each direction, preferably 5 times, with the orientation temperature being from 130° to 150° C., with 130° C. being preferred.

In the polypropylene/glass beads system, the amount of the filler should be in the range of 55 to 65% by weight of the composition, preferably 65%. In this system the amount of calcium stearate should be 0.1 to 3.0% by weight, preferably 0.5 to 2.0%. This film should be biaxially oriented by stretching from 4 to 7 times in each direction, with 5 times being the preferred stretching, at a temperature of from 130 to 150° C., preferably 135° C.

In the polybutylene/calcium carbonate system, the amount of the filler should be in the range of 65 to 75% by weight of the composition, with 70% being preferred; in this system the amount of calcium stearate to be used should be in the range of 0.2 to 4% by weight, with 2% being preferred. This film should be biaxially oriented from 1.5 to 5 times, preferably 4 times, at a temperature range of 20° to 105° C., 100° C. being preferred.

In the polyethylene/calcium carbonate system, the amount of filler should be in the range of 60 to 70% by weight, 70% being preferred. The amount of calcium stearate in this system should be from 0.1 to 3.5%, 0.5 to 2% being preferred. This film should be biaxially oriented 1.5 to 5 times, with 4 times being preferred, in a temperature range of 20° to 110° C., with 100° C. being preferred. A blend of linear low density polyethylene and polypropylene in a ratio of 95 to 5 can improve processability by reducing die line problems compared to the use of linear low density polyethylene (LLDPE) alone.

A blend of polypropylene with ethylene-propylene copolymer can be processed more readily than a similar composition which contains polypropylene as the sole polymer. When glass beads are used instead of the calcium carbonate as the filler, the films are useful as battery separators.

The particle size of the filler ultimately determines the pore size of the microporous films of this invention. Thus, smaller particle sizes of fillers permit attainment of smaller pores compared to larger particle sizes of fillers at equal loading and equal overall porosity. There is no theoretical limitation on the size of the fillers which may be used in the practice of this invention. However, practical considerations impose effective limitations. In the present invention, it has been found that fillers of particle size ranging from 10 to 25 micrometers in mean diameter are preferred over smaller particle size fillers in order to attain the high breathability of the instant film. The preferred particle size of the calcium carbonate filler is about 12.5 micrometers mean diameter.

Filler loading determines to a great extent how far the precursor film must be stretched to attain a given degree of overall porosity. Below the lower end of the loading range, the pores are less numerous and less interconnected; therefore, the film is less permeable at a given draw ratio than when a higher filler loading is employed. Above the higher end of the loading range, either the materials will not blend uniformly or the casting made from the composition will not stretch. The preferred loading in the present invention is about 60 to 75% by weight of the comPosition, preferably 65% to 75%. Although other inorganic fillers may be used, calcium carbonate is preferred.

Stabilizers are usually used in the composition of the present invention in the range of from 0.1 to 2% by weight as a means to insure stabilization of the system to UV light, oxygen, and heat; it is especially useful in the systems with the polypropylene and the polyethylene.

A critical requirement in the process of this invention is to maintain the moisture level in the composition below 700 ppm prior to extruding the casting so as to create a casting with a smooth surface. A smooth surface is necessary to enable the casting to be stretched uniformly.

After the film composition is prepared, it may be compounded into the film of this invention by any known method suitable for the melt blending of thermoplastic polymers at temperatures at which the matrix polymers are processible. High shear mixing, which can be achieved in a Banbury-type or another high intensity mixer or in continuous mixers such as extruders, is preferred. There is no need to premix ingredients, but this may be done without detriment to the practice of this invention and may in certain instances offer improved performance.

After the ingredients of the composition of this invention have been melt blended, the moisture level of this blend is then maintained below 700 parts per million (ppm) (preferably below 300 ppm). A preferred method for maintaining the moisture content at the desired levels is to cool extruded strands on a moving conveyor belt using flowing air. This air-cooling method yields strands and pellets which have residual moisture levels far below the levels achieved by the water-bath-cooling process typical in the industry.

The strands were then pelletized using conventional techniques in the industry. To accurately achieve this moisture level, sensitive moisture measurement techniques are required. For example, a Coulometric Karl Fischer titration method (using the Brinkman Model 652 RF Coulometer) was used successfully for verifying the desired moisture level in the formulations.

After blending and maintaining the moisture level, the composition is converted into any convenient form for processing into film, including pellets or sheets. The film fabrication ca be accomplished by any convenient technique including compression molding, flat film extrusion, or blown film extrusion.

After the film is fabricated into its desired form, it is then biaxially oriented by stretching by any of the well known techniques in the art including, by hydraulics, by pinch rolls moving at different rates, or by tentering. Biaxial stretching can be performed sequentially or simultaneously. Sequential biaxial stretching is preferred when using the tentering operation.

Another process of maintaining the desired moisture level is to emploY vacuum-drying in order to reduce the moisture level in too-wet pellets to acceptable levels (below 700 ppm, and preferably below 300 ppm). In this case, pellets composed of polymer plus filler would be made using a water-bath-cooling process such that the residual moisture level is excessive. These too-wet pellets can be subjected to a partial vacuum, preferably with some heating to speed the process, for a period of time until the moisture content is within acceptable limits as defined above. This process works but is not the preferred one since an extra process, vacuumdrying, is required.

Yet another process of maintaining the desired moisture level is by charging the hot melt directly to the extruder which extrudes the casting from a die. In this case, the molten composition is never exposed to liquid water and, thus, has a low residual moisture level as defined above. Therefore, a smooth and highly-orientable casting will be formed.

The stretch ratio of at least two times the original forming dimensions is significant to producing a film having at least 30% of pores resulting in relatively high density films. However, to produce relatively low density films, it is preferred that the film be stretched to at least 3 to 8 times its original forming dimensions in mutually perpendicular directions, resulting in a film having about 40 to 70% pores.

Stretching is effected above the glass transition temperature of the matrix polymer (preferably at least 20° C. above) and below the melting temperature of the matrix polymer, especially within 10° C. of that temperature, depending to some degree on the rate of stretching. Different polymers and compositions thereof exhibit different elastic and viscoelastic behavior. Thus, different amounts of stretching must be imposed on different samples in order to obtain the same permeability properties. Nevertheless, the film must be stretched beyond its yield point in order to attain the permanent deformation necessary for the formation of porosity.

For a given composition, a greater degree of stretch results in greater overall porosity. Higher overall porosity can be attained by adding more filler and stretching, the same amount or less.

In the following examples, all parts, proportions, and percentages are by weight unless otherwise indicated.

Examples 1–14

In Examples 1–8, the ingredients (listed in Table 1) were blended at room temperature and compounded in a twin-screw extruder; strands were extruded at in a temperature range of 243° to 265° C. The strands were then air cooled (except in Examples 6–8 that were water cooled) and pelletized. The pellets were vacuum dried for 24 hours at 80° C. (except Examples 7 and 8 that were vacuum dried for 8 hours at 70° C. Using a melt temperature of 478° to 540° F., the pellets were extruded by a single screw extruder through a six inch wide slit die onto a casting roll maintained at about 65° C. (except Examples 6–8 were maintained at about 18° –24° C.) so as to form a 15 mil thick casting. Using a T. M. Long stretcher, square pieces having the dimensions 2×2 inches from the casting were biaxially oriented by stretching 4 times in the machine direction and 4 times in the transverse direction (except Example 8 was stretched 2× by 2×) at 100° C., producing the product as set forth in the following Table 1.

In Examples 9 and 10, the ingredients were blended together on a 2-roll mill at 200° C.; this blend was compression molded at 215° C. to yield 30 mil thick plaques. Two inch by two inch portions of the plaques were biaxially oriented by stretching 5 times in the machine direction and 5 times in the transverse direction on a T. M. Long stretcher at 140° C. to make the film as described in Table 1.

In Examples 11 and 14, the ingredients were compounded in a twin screw extruder at 225° –250° C.; the extrudate was pelletized and cast on a casting extruder at 180° –230° C. For Example 11 since much strand breakage and non-uniformity was observed during the pelletizing step, the casting could not be stretched at 140° C. on the T. M. Long stretcher; the casting was too brittle. For Example 14, 2×2 inch portions of the casting were stretched 4.5× by 4.5× at 140° C. on the T. M. Long stretcher.

In Example 12 and 13, the ingredients were blended by a twin-screw extruder and were extruded by a single screw extruder and slit die to form a 30 mil casting; the casting was stretched 5× by 5× on a T. M. Long stretcher to form the film.

TABLE 1

| | | 1a,b,c | 2 | 3 | Com 4 | 5 | 6 | 6 | Com 7 | Com 8 | 9 | Com 10 | 11 | 12 | 13 | 14 |
|---|---|---|---|---|---|---|---|---|---|---|---|---|---|---|---|---|
| POLYMER (%) | | LLDPE | LLDPE | LLDPE | LLDPE | LLDPE/PP | LLDPE/PP | PB | PB | PB | PP/C₂C₃* (1:1) | PP/C₂C₃ (1:1) | PP | PP/C₂C₃ | PP/C₂C₃ (1:1) | PP (1:1) |
| | | 28.5 | 33.25 | 38.0 | 29.4 | 27.0/1.5 | 28.5/1.5 | 50.0 | 30.0 | 39.83 | 49.74 | 39.64 | 34.61 | 34.91 | 36.05 |
| CALCIUM STEARATE (%) | | 1.5 | 1.75 | 2.0 | 0.6 | 1.5 | | 0 | 0 | 0.32 | 0.40 | 0.40 | 1.04 | 0.17 | 1.09 |
| CaCO₃ (%) | | 70 | 65 | 60 | 70 | 70 | 70 | 50 | 70 | 59.75 | 49.74 | 59.46 | 64.27 | 64.83 | — |
| STABILIZER | | | | | | | | | | 0.10 | 0.12 | 0.50 | 0.09 | 0.09 | 0.16 |
| GLASS BEADS (%) | | | | | | | | | | | | | | | 62.71 |
| PRODUCT PROPERTIES | | | | | | | | | | | | | | | | |
| | | 1a,b,c | 2 | 3 | Com 4 | 5 | 6 | Com 7 | Com 8 | 9 | Com 10 | 11 | 12 | 13 | 14 |
| ORIENTATION/ TEMP °C. | a | 4× by 4×/ 100° C. | 4× by 4×/ 100° C. | 4× by 4×/ 100° C. | Mat'ls. would not mix well | 4× by 4×/ 100° C. | 4× by 4×/ 100° C. | 4× by 4× 100° C. | 2× by 2× 100° C. | 5× by 5×/ 140° C. | 5× by 5× 140° C. | would not stretch 140° C. | 5× by 5× | 5× by 5× | 4.5× by 4.5×/ 140° C. |
| | b | 3× by 3× 100° C. | | | | | | | | | | | | | |
| | c | 2× by 2×/ 100° C. | | | | | | | | | | | | | |
| FILM THICK-NESS (mil) | a = | 2.5 | 3.0 | 3.5 | | 3.0 | 4.0 | 3.0 | | | | | | | |
| | b = | 6.0 | | | | | | | | | | | | | |
| | c = | 10.5 | | | | | | | | | | | | | |
| % AIR VOIDS | a = | 65 | 66 | 61 | | | 60 | | | | | | | | |
| | b = | 65 | | | | | | | | | | | | | |
| | c = | 65 | | | | | | | | | | | | | |
| Gurley POROSITY (METHOD B) | a = | 0.1 sec | 0.5 sec | 0.8 sec | | 0.3 sec | 1.4 sec | >30 sec | | 85 sec | >10 min | | >20 sec | | 4.0 sec |
| | b = | 0.2 sec | | | | | | | | | | | | | |
| | c = | 0.4 sec | | | | | | | | | | | | | |

*C₂C₃ is an ethylene-propylene copolymer containing 2.7 mole percent ethylene units.

All of the resulting products of the Examples were opaque white films.

Examples 1a, b, and c show that for the system LLDPE/ CaCO$_3$ films, 70% by weight of the filler gives much lower Gurley number (i.e., high breathability) than 65% by weight of the filler. Examples 1a, b and c show that breathability is the best in the more highly oriented films. Similarly, 65% by weight of the filler (Example 2 gives a much lower Gurley number than 60% filler, (Example 3). Example 4 compared to Example 1 shows that the processibility of the formulation is improved by adding 1.5% of calcium stearate (Example 1) instead of 0.6% calcium stearate (Example 4); further, in comparative Example 4, die deposits and melt fractures were excessive and caused constant breakage of the extruded molten strands. Thus, the material could not be pelletized and extruded into castings suitable for orientation. Example 5 demonstrates the advantage of using a small amount of polypropylene additive in the LLDPE to reduce die lines. Regions of melt fracture (die lines) thinner than the rest of the casting were greatly reduced compared to the melt fracture regions commonly observed in compositions such as those in Examples 1a, b and c.

Example 6 shows that, for polybutene/calcium carbonate film, 70% by weight of the filler gives much lower Gurley number (i.e., high breathability) than 50% by weight of the filler in Example 7. Example 8, compared to Example 6, shows that 1.5% of calcium stearate allows much easier processing to a porous film than if no calcium stearate is used (Example 8). The film prepared in comparative Example 8 had many visible pinholes and was extremely rough. Gurley measurements were not possible. Castings made from this composition could not be oriented 4 times by 4 times at the temperature of 100° C. Example 9 shows that, for polypropylene/calcium carbonate films, 60% by weight of the filler gives a much lower Gurley number than when only 50% by weight of the filler is used (Example 10). Example 11 compared to Example 9, shows that using a blend of polypropylene and ethylene-propylene copolymer gives better processing than if pure polypropylene is substituted for the blend (Example 11) because the casting of Example 11 would not stretch to form film at 140° C. Example 12 shows that high calcium stearate levels greatly improves processability compared to a low calcium stearate level in Example 13 because the resulting film had large visible pin holes and was extremely rough. Example 14 demonstrates a breathable composition composed of polypropylene and glass bead filler.

EXAMPLE 15

A series of experiments were run on strawberries, mushrooms and broccoli to demonstrate the reduced loss of water vapor from the produce while not interfering with the respiration of the produce using a container sealed with the breathable film of the instant invention. The container was constructed of a substantially gas-impermeable material having a window in the top with a gas-permeable panel of a material of this invention therein to provide a substantially free flow therethrough of the O$_2$ and CO$_2$ gases yet substantially no flow of water vapor. The details and results of the experiments are as follows:

| PRODUCE (g) | FILM TYPE & PERMEANCE (cc/100 in$^2$-atm-day) | TIME IN PACKAGE (HR) TEMP (°C.) | % WEIGHT LOSS | STEADY-STATE O$_2$ % | STEADY-STATE CO$_2$ % |
|---|---|---|---|---|---|
| Strawberries (652 g) | Biaxial PP/60% Atomite. Permeance 100 Million | 310 (4°) | 0.1 | 16 | 6 |
| Strawberries (625 g) | Control (Open To Atmosphere) | 165 (4°) | 14.7 | 21 | 0 |
| Mushrooms (190 g) | Biaxial PP/60% Atomite. Permeance 100 million | 145 (4°) | 0.4 | 20 | 2 |
| Mushrooms (190 g) | Control (open) | 167 (4°) | 33 | 21 | 0 |
| Broccoli (247 g) | Biaxial PP/60% Atomite. Permeance 100 million | 318 (11°) | 11.5 | 19 | 3 |
| Broccoli (247 g) | Control (open) | 318 (11°) | 33 | 21 | 0 |

These experiments demonstrate that a breathable film of this invention placed over an aperture (window) in a substantially gas-impermeable container of produce will reduce the rate of evaporation, which is beneficial, without necessarily inducing major changes in the O$_2$ and CO$_2$ levels in the package. The crispness or appearance of the strawberries, mushrooms, and borccoli was improved by the use of the breathable film.

What I claim and desire to protect by Letters Patent:

1. A method of preparing a breathable microporous polymeric film having the composition of 20–37% by weight of a polymer or copolymer of an α-olefin having 1–8 carbons or mixtures thereof, 60–75% by weight of calcium carbonate or glass beads, 0.1–3.0% by weight of calcium stearate and, optionally, 0–2% by weight of a UV light, oxygen, and heat stabilizer by preparing a melt blend of the ingredients, maintaining the moisture level in the melt blend below 700 ppm prior to extruding a casting, and based on the polymer or copolymer used, stretching the casting in two directions of from 1.5 to 7 times in each direction in a temperature range of from about 20° to about 160° C. thereby producing the breathable microporous film having a Gurley Porosity of from 0.1 to 85 seconds so that the film has good air and water vapor transmission rates but is substantially imPenetrable by liquid water.

2. The method of claim 1 wherein the moisture level is maintained below 300 ppm.

3. The method of claim 2 wherein the composition has 65 to 75% of calcium carbonate.

4. The method of claim 3 wherein the polymer is polyethylene or polybutylene and the casting is stretched in two directions from 1.5 to 5 times in each direction in a temperature range of from about 20° to about 105° C.

5. The method of claim 3 wherein the polymer is polypropylene and the casting is stretched in two directions from 4 to 7 times in each direction in a temperature range of from about 130° to about 160° C.

* * * * *

UNITED STATES PATENT AND TRADEMARK OFFICE
CERTIFICATE OF CORRECTION

PATENT NO. : 4,923,650
DATED : May 8, 1990
INVENTOR(S) : Antoon & Hill

It is certified that error appears in the above-identified patent and that said Letters Patent is hereby corrected as shown below:

Column 2, line 39 " cc/100in "

should read -- $cc/100in^2$ --

Column 4, line 39 " ca "

should read -- can --

Column 6, line 1 after " 8 hours at 70° C. "

should read -- 70° C.) --

Column 9, line 9 " (Example 2 "

should read -- (Example 2) --

Signed and Sealed this

Sixth Day of August, 1991

*Attest:*

HARRY F. MANBECK, JR.

*Attesting Officer*     *Commissioner of Patents and Trademarks*